United States Patent
Schendel (10) Patent No.: US 9,296,781 B2
(45) Date of Patent: Mar. 29, 2016

(54) SYSTEM AND METHOD FOR COLLAGEN ISOLATION

(75) Inventor: Stephen Schendel, Menlo Park, CA (US)

(73) Assignee: VERIS MEDICAL, INC., E. Palo Alto, CA (US)

( * ) Notice: Subject to any disclaimer, the term of this patent is extended or adjusted under 35 U.S.C. 154(b) by 0 days.

(21) Appl. No.: 14/125,632

(22) PCT Filed: Jun. 22, 2012

(86) PCT No.: PCT/US2012/043765
§ 371 (c)(1),
(2), (4) Date: Dec. 12, 2013

(87) PCT Pub. No.: WO2013/003229
PCT Pub. Date: Jan. 3, 2013

(65) Prior Publication Data
US 2014/0105856 A1 Apr. 17, 2014

Related U.S. Application Data

(60) Provisional application No. 61/501,946, filed on Jun. 28, 2011.

(51) Int. Cl.
| | | |
|---|---|---|
| C07K 1/30 | (2006.01) | |
| C07K 14/78 | (2006.01) | |
| A61K 35/35 | (2015.01) | |
| A61K 38/39 | (2006.01) | |
| C07K 1/14 | (2006.01) | |
| C08H 1/06 | (2006.01) | |
| C08L 89/06 | (2006.01) | |
| A61K 8/65 | (2006.01) | |
| A61Q 19/08 | (2006.01) | |
| A61K 8/98 | (2006.01) | |
| A61K 45/06 | (2006.01) | |
| A61K 35/28 | (2015.01) | |
| A61Q 19/00 | (2006.01) | |
| A61K 38/00 | (2006.01) | |

(52) U.S. Cl.
CPC . *C07K 1/145* (2013.01); *A61K 8/65* (2013.01); *A61K 8/981* (2013.01); *A61K 35/28* (2013.01); *A61K 35/35* (2013.01); *A61K 38/39* (2013.01); *A61K 45/06* (2013.01); *A61Q 19/00* (2013.01); *A61Q 19/08* (2013.01); *C07K 14/78* (2013.01); *C08H 1/06* (2013.01); *C08L 89/06* (2013.01)

(58) Field of Classification Search
CPC .............. C07K 1/14; C07K 1/34; C07K 14/47
See application file for complete search history.

(56) References Cited

U.S. PATENT DOCUMENTS

| | | | |
|---|---|---|---|
| 5,110,604 A * | 5/1992 | Chu et al. | 424/484 |
| 5,244,458 A * | 9/1993 | Takasu | 604/22 |
| 5,261,612 A | 11/1993 | Ftaiha | |
| 6,387,380 B1 | 5/2002 | Knowlton | |
| 6,933,326 B1 | 8/2005 | Griffey et al. | |
| 7,588,732 B2 | 9/2009 | Buss | |
| 8,459,121 B2 * | 6/2013 | Laugharn et al. | 73/644 |
| 2003/0028228 A1 * | 2/2003 | Sand | 607/89 |
| 2004/0087016 A1 * | 5/2004 | Keating et al. | 435/366 |
| 2006/0051865 A1 | 3/2006 | Higgins et al. | |
| 2007/0104695 A1 * | 5/2007 | Quijano et al. | 424/93.7 |
| 2008/0319417 A1 * | 12/2008 | Quijano et al. | 604/522 |
| 2009/0175922 A1 * | 7/2009 | Voytik-Harbin | 424/423 |
| 2011/0020271 A1 | 1/2011 | Niklason et al. | |
| 2011/0020864 A1 | 1/2011 | Huang | |

FOREIGN PATENT DOCUMENTS

| | | |
|---|---|---|
| EP | 0418979 A2 | 3/1991 |
| EP | 0515726 A1 | 8/1991 |
| EP | 448770 A1 * | 10/1991 |
| WO | 2008143402 A1 | 11/2008 |
| WO | 2010021993 A1 | 2/2010 |

OTHER PUBLICATIONS

Divoux et al. (2010) Fibrosis in Human Adipose Tissue: Composition, Distribution, and Link With Lipid Metabolism and Fat Mass Loss, Diabetes, vol. 59, No. 11, pp. 2817-2825.*
Australian Patent Office (ISA) International Search Report and Written Opinion for PCT/US2012/043765 dated Aug. 14, 20012.
Li, D., et al, "Ultrasonic irradiation in the enzymatic extraction of collagen," Ultrason Sonochem, Jun. 2009, 16(5):605-9.
Extended European Search Report and Supplementary European Search Report dated Dec. 4, 2014 for application No. EP12805406.

* cited by examiner

*Primary Examiner* — Anand Desai
*Assistant Examiner* — Samuel Liu
(74) *Attorney, Agent, or Firm* — Edwin S. Flores; Chalker Flores, LLP (57) ABSTRACT

System and methods for isolation of collagen and other fibrous tissue from adipose tissue are described herein. The method of the present invention isolates the collagen from adipose tissue by sonication. The tissue to be sonicated is placed in a container or a flow cell transparent to ultrasound waves. After sonication the sonicated material is filtered out through the bottom of the flow cell and the sonicated collagen is trapped in the filter, which may be taken for further processing. The isolated collagen can then be combined with a suitable carrier for re-injection to correct various tissue defects such as wrinkles, to form a carrier for the stem cells, a filler, and matrix for new collagen production by injecting into the desired area of the host.

23 Claims, 2 Drawing Sheets

SYSTEM AND METHOD FOR COLLAGEN ISOLATION

CROSS-REFERENCE TO RELATED APPLICATIONS

This application is a National Stage of International Application No. PCT/US2012/043765, filed Jun. 22, 2012, which claims priority to and the benefit of U.S. Provisional Patent Application Ser. No. 61/501,946, filed Jun. 28, 2011. The contents of each of which are incorporated by reference in their entirety.

STATEMENT OF FEDERALLY FUNDED RESEARCH

None.

TECHNICAL FIELD OF THE INVENTION

The present invention relates in general to the field of cosmetic, reconstructive surgery, or both and more particularly, to an ultrasound system and method for isolation of collagen and other fibrous tissue from adipose tissue.

BACKGROUND OF THE INVENTION

Without limiting the scope of the invention, its background is described in connection with methods and systems for deriving collagen and fibrous tissue.

For example, U.S. Pat. No. 5,261,612 issued to Fataiha (1993) discloses a method and apparatus for extracting injectable collagen from human adipose tissue, such as removed by liposuction procedures. The apparatus of the '612 patent includes a clear container with inlet and outlet fittings to be attached to the suction line of a liposuction machine to collect globules of adipose tissue. The container has a needle-like rod disposed in its center and an electric motor and belt drive to rotate the rod at a speed sufficient to cause interstitial reticular fiber from adipose tissue to adhere to and wrap around the rod. Water may then be flowed in through the inlet fitting and drawn out through the outlet fitting to flush the adipose tissue out of container, leaving the reticular fibers on the rod. The rod is then retracted (lowered) through a sleeve which has a rotating chopping blade, scrapping the fiber into a cup area of chopping blades. A pharmaceutical carrier such as saline solution is injected into the container. The rotating chopping blades are driven by the motor and belt to emulsify the reticular fibers into the saline solution. The emulsion is then extracted for use as injectable collagen.

U.S. Pat. No. 7,588,732 issued to Buss (2009) discloses an autologous tissue harvesting and irrigation device a method and a kit for the collection of viable fat cells and/or adipose tissue with decreased handing and improved yield and viability. According to the '732 patent the cell harvesting device comprises: a housing comprising a portal located at a proximal end of the housing; a filter chamber assembly connected to the portal and disposed within the housing and having an exterior and an interior, wherein interior of the filter chamber assembly is in fluid communication with the portal; a plunger tube slideably engaged within the filter chamber assembly, the plunger tube comprising a plunger at its proximal end, the plunger disposed within the filter chamber assembly, and wherein the plunger tube has one or more openings that allows fluid communication between the portal, the exterior of the filter chamber assembly and the interior of the plunger tube; and a tubing interface located at the distal end of the plunger tube.

Another example is taught in U.S. Patent Publication No. 20110020864 (Huang, 2011) which discloses a method of preparing collagen by first producing a collagen matrix and then extracting collagen from the matrix. The method taught in the Huang invention comprises the steps of: (i) providing a connective tissue having a surface ranging from 20 mm2 to 2 m2, (ii) swelling the connective tissue with a first acidic solution by at least 50% in volume to form a swollen connective tissue, wherein the acidic solution is substantially free of salt and has a pH of 1-6, (iii) washing the swollen connective tissue to remove non-collagenous material, thereby producing a collagen matrix, and (iv) extracting collagen from the collagen matrix with an extraction solution to produce a collagen-containing solution.

A cryofractionation method for processing an acellular tissue matrix to give a particulate acellular tissue matrix is described in U.S. Pat. No. 6,933,326 issued to Griffey et al. (2005). The Griffey method includes: cutting sheets of dry acellular tissue matrix into strips; cryofracturing the dry acellular tissue matrix strips at cryogenic temperatures; separating the resulting particles by size at cryogenic temperatures; and freeze drying the fraction of particles desired size to remove any moisture that may have been absorbed to give a dry particulate acellular tissue matrix. Rehydration of the dry particulate acellular tissue matrix may take place just prior to use. The particulate acellular tissue may be applied to a recipient site, by way of injection, spraying, layering, packing, in-casing, or any combinations thereof. The particulate acellular tissue may further include growth and stimulating agents, other pharmaceutically active compounds, and may also be combined with stem cells.

Finally, U.S. Patent Publication No. 20110020271 (Niklason et al. 2011) describes methods for elastin (a type of collagen) production. The Niklason invention provides methods and kits for soft tissue augmentation, including compositions comprising isolated elastin and a pharmaceutically acceptable carrier wherein the human elastin is substantially insoluble in water with a molecular weight greater than 100 kDa.

SUMMARY OF THE INVENTION

The present invention provides a system and method that involves sonication for the isolation of collagen and other fibrous material from adipose tissue. The collagen isolated by the method of the present invention can be used in the treatment of chronic wounds, as a carrier for stem cells or by itself, for e.g., in ureter surgery for urinary incontinence as bovine collagen is used now, to fill wrinkles or soft tissue defects for medical or cosmetic purposes.

In one embodiment the present invention discloses a method for isolation of one or more connective tissue proteins from one or more fat containing tissues comprising the steps of: (i) providing or flowing the fat containing tissue harvested by liposuction, abdominoplasty, or any other fat removal techniques in a container or a flow cell, wherein the container or the flow cell is an acoustically permeable closed system and further comprises a filter, (ii) exposing the fat containing tissue to one or more acoustic pulses to separate the one or more connective tissue proteins from a stromal vascular fraction (SVF), wherein the SVF comprises lipids, cells, or any other extracellular elements, and (iii) isolating the separated connective tissue proteins.

The connective tissue protein isolated using the method disclosed hereinabove comprises at least one of collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, collagen type XXIX, or elastin. In a specific aspect the isolated connective tissue protein comprises collagen type I. In another aspect the one or more fat containing tissues comprises adipose tissue, dermis, and other microvascular tissues including placenta or muscle. In other specific aspects of the method disclosed hereinabove the one or more fat containing tissues comprises adipose tissue and the acoustic pulses comprise ultrasonic waves. In another aspect the method of isolating the connective tissue proteins is performed under sterile conditions. In yet another aspect the frequency for the one or more ultrasonic pulses ranges from 40-500 kHz. In another aspect a pore size of the filter ranges from 5 microns-300 microns. It will be understood by the skilled artisan that the ultrasonic pulse and the pore size ranges hereinabove are non-limiting and that the method of the present invention can be performed using pulse ranges and pore sizes that vary considerably from what is listed herein.

The isolation method as described hereinabove further comprising the optional steps of: (i) reconstituting the one or more isolated connective tissue proteins in vehicle or diluent, wherein the vehicle or diluent is selected from the group consisting of water, buffer, saline, serum and other body fluids, and any combinations thereof, (ii) processing the one or more isolated connective tissue proteins for long-term storage using one or more cryogenic processes (cryofreezing) with one or more optional preservatives, (iii) combining the one or more isolated connective tissue proteins with one or more pharmacologically active or inactive additives selected from at least one of epidermal growth factor, fibroblast growth factor (FGF), nerve growth factor, keratinocyte growth factor, platelet derived growth factor (PDGF), vasoactive intestinal peptide, stem cell factor, vascular endothelial growth factor (VEGF), bone morphogenic proteins, chondrocyte growth factor, analgesic drugs, hemostatic drugs, antibiotic drugs, antioxidants, heparin, anti-inflammatory drugs, local anesthetics, tissue formation agents, adipose tissue formation agents, transforming growth factor, transforming growth factor-β, connective tissue activating peptides, β-thromboglobulin, insulin-like growth factors, tumor necrosis factors, interleukins, colony stimulating factors, erythropoietin, nerve growth factors, interferons, mesenchymal stem cells, epidermal stem cells, cartilage stem cells, adipose derived stem cells (ASCs), hematopoietic stem cells, and any combinations thereof, and (iv) injecting the one or more isolated connective tissue proteins to perform or enhance effectiveness of one or more cosmetic surgery procedures, wherein the one or more cosmetic surgery procedures selected from the group consisting of treatment of wrinkles, deep folds, frown lines, deep scars, lip tissue augmentation, wound healing, facial rejuvenation, regeneration and tissue engineering, cleft palate surgery, carrier for stem cells, filler and matrix for new collagen production, and other combinations and modifications thereof. In another aspect, the fat containing tissue is heterologous tissue. In another aspect, the method further comprises the step of morselizing the tissue prior to reinjection into a host or use in vitro.

In another embodiment the present invention relates to a composition for use in one or more cosmetic surgery procedures in a subject comprising: one or more connective tissue proteins derived or isolated from one or more fat containing tissues, wherein the connective tissue proteins are isolated by a method comprising the steps of: (a) providing or flowing the fat containing tissue harvested by liposuction, abdominoplasty, or any other fat removal techniques in a container or a flow cell, wherein the container or the flow cell is an acoustically transparent closed system and further comprises a filter, (b) exposing the fat containing tissue to one or more acoustic pulses to separate the one or more connective tissue proteins from a stromal vascular fraction (SVF), wherein the SVF comprises lipids, cells, or any other extracellular elements; and (c) isolating the separated connective tissue proteins from the SVF; and an optional vehicle or medium for dissolving, dispersing, or suspending the one or more tissue proteins, wherein the vehicle or medium is selected from the group consisting of water, buffer, saline, serum and other body fluids, and any combinations thereof.

The composition as disclosed hereinabove may comprise one or more pharmacologically active or inactive additives selected from the group consisting of epidermal growth factor, fibroblast growth factor (FGF), nerve growth factor, keratinocyte growth factor, platelet derived growth factor (PDGF), vasoactive intestinal peptide, vascular endothelial growth factor (VEGF), stem cell factor, bone morphogenic proteins, chondrocyte growth factor, analgesic drugs, hemostatic drugs, antibiotic drugs, antioxidants, heparin, anti-inflammatory drugs, local anesthetics, tissue formation agents, adipose tissue formation agents, transforming growth factor, transforming growth factor-β, connective tissue activating peptides, β-thromboglobulin, insulin-like growth factors, tumor necrosis factors, interleukins, colony stimulating factors, erythropoietin, nerve growth factors, interferons, mesenchymal stem cells, epidermal stem cells, cartilage stem cells, adipose derived stem cells (ASCs), hematopoietic stem cells, and any combinations thereof.

The composition as described in the above embodiment can be adapted for use in one or more cosmetic surgery procedures selected from the group consisting of treatment of wrinkles, deep folds, frown lines, deep scars, lip tissue augmentation, wound healing, facial rejuvenation, regeneration and tissue engineering, cleft palate surgery, dermal fillers, carrier for stem cells, filler and matrix for new collagen production, and other combinations and modifications thereof. In one aspect of the composition described above the connective tissue protein comprises collagen. In another aspect the one or more fat containing tissues comprises adipose tissue, dermis, and other microvascular tissues including placenta or muscle. In yet another aspect the acoustic pulses comprise frequencies ranging from subaudio to ultrasonic waves. More specifically, the acoustic pulses comprise ultrasonic waves, wherein a source of the one or more acoustic pulses comprises acoustic horns, transducers, piezo-electric crystals, a sonicating probe, or any combinations thereof. In one aspect the method of isolating the connective tissue proteins is performed under sterile conditions. In related aspects the frequency for the one or more ultrasonic pulses ranges from 40-500 kHz and a pore size of the filter ranges from 5 microns-300 microns. In another aspect a concentration of the optional vehicle or medium in the composition ranges from 10% to 60%. In another aspect, the composition is formed into a scaffold for seeding of cells into the scaffold.

In yet another embodiment the present invention provides a method for performing, enhancing effectiveness of a cosmetic surgery procedure, or both in a subject comprising the steps of: identifying the subject in need of the cosmetic surgery procedure, enhanced effectiveness of the cosmetic surgery procedure, or both and injecting an effective amount of a composition comprising one or more connective tissue proteins derived or isolated from one or more fat containing tissues and an optional vehicle or medium for dissolving, dispersing, or suspending the one or more tissue proteins, wherein the vehicle or medium is selected from the group consisting of water, buffer, saline, serum and other body fluids, and any combinations thereof. The connective tissue proteins described in the method herein are isolated by a method comprising the steps of: providing or flowing the fat containing tissue harvested by liposuction, abdominoplasty, or any other fat removal techniques in a container or a flow cell, wherein the container or the flow cell is a transparent closed system and further comprises a filter, exposing the fat containing tissue to one or more acoustic pulses to separate the one or more connective tissue proteins from a stromal vascular fraction (SVF), wherein the SVF comprises lipids, cells, or any other extracellular elements; isolating the separated connective tissue proteins from the SVF. In another aspect, the fat containing tissue is heterologous tissue. In another aspect, the method further comprises the step of morselizing the tissue prior to reinjection into a host or use in vitro.

In one embodiment the present invention describes a sterile process for collagen isolation from adipose tissue comprising the steps of: providing fat containing adipose tissue harvested by liposuction, abdominoplasty, or any other fat removal techniques in a container, wherein the container comprises a filter and is transparent to permit a passage of one or more ultrasonic waves or pulses and may be a closed system, exposing the fat containing tissue to one or more ultrasonic waves or pulses to separate the collagen and an extracellular matrix (ECM) from a stromal vascular fraction (SVF), wherein the SVF comprises lipids, cells, or any other extracellular elements, and isolating the separated collagen and ECM from the SVF.

The method described hereinabove further comprising the optional steps of: separating the isolated collagen from the ECM by one or more physical separation techniques selected from the group consisting of centrifugation, filtration, ultrasonic separation, or any combinations thereof, processing the collagen for long-term storage using one or more cryogenic processes with one or more optional preservatives, reconstituting the isolated collagen in a vehicle or diluent, wherein the vehicle or diluent is selected from the group consisting of water, buffer, saline, serum and other body fluids, and any combinations thereof, combining the isolated collagen with one or more pharmacologically active or inactive additives selected from the group consisting of epidermal growth factor, fibroblast growth factor (FGF), nerve growth factor, keratinocyte growth factor, platelet derived growth factor (PDGF), vasoactive intestinal peptide, vascular endothelial growth factor (VEGF), stem cell factor, bone morphogenic proteins, chondrocyte growth factor, analgesic drugs, hemostatic drugs, antibiotic drugs, antioxidants, heparin, anti-inflammatory drugs, local anesthetics, tissue formation agents, adipose tissue formation agents, transforming growth factor, transforming growth factor-β, connective tissue activating peptides, β-thromboglobulin, insulin-like growth factors, tumor necrosis factors, interleukins, colony stimulating factors, erythropoietin, nerve growth factors, interferons, mesenchymal stem cells, epidermal stem cells, cartilage stem cells, adipose derived stem cells (ASCs), hematopoietic stem cells, and any combinations thereof, and injecting the isolated collagen to perform or enhance effectiveness of one or more cosmetic surgery procedures, wherein the one or more cosmetic surgery procedures selected from the group consisting of treatment of wrinkles, deep folds, frown lines, deep scars, lip tissue augmentation, wound healing, facial rejuvenation, regeneration and tissue engineering, cleft palate surgery, carrier for stem cells, filler and matrix for new collagen production, and other combinations and modifications thereof. In another aspect, the fat containing tissue is heterologous tissue. In another aspect, the method further comprises the step of morselizing the tissue prior to reinjection into a host or use in vitro.

Another embodiment of the present invention relates to a sterile process for collagen isolation from adipose tissue comprising the steps of: providing fat containing adipose tissue harvested by liposuction, abdominoplasty, or any other fat removal techniques in a flow cell comprising a filter, wherein the adipose tissue is pumped or continuously flows into the flow cell, wherein the flow cell is permeable to one or more ultrasonic waves or pulses and may be a closed system, exposing the fat containing tissue to one or more ultrasonic waves or pulses to separate the collagen and an extracellular matrix (ECM) from a stromal vascular fraction (SVF), wherein the SVF comprises lipids, cells, or any other extracellular elements, and isolating the separated collagen and ECM from the SVF.

The present invention also discloses a composition for use in one or more cosmetic surgery procedures in a subject comprising: collagen derived or isolated from one or more adipose tissues optionally dissolved, dispersed, or suspended in a suitable vehicle or diluent, wherein the vehicle or diluent is selected from the group consisting of water, buffer, saline, serum and other body fluids, and any combinations thereof. The composition described herein is made by the method described previously hereinabove. In another aspect, the composition is formed into a scaffold for seeding of cells into the scaffold.

In yet another embodiment the present invention relates to a method for performing, enhancing effectiveness of a cosmetic surgery procedure, or both in a subject comprising the steps of: identifying the subject in need of the cosmetic surgery procedure, enhanced effectiveness of the cosmetic surgery procedure, or both; and injecting an effective amount of a composition comprising collagen derived or isolated from one or more adipose tissues optionally dissolved, dispersed, or suspended in a suitable vehicle or diluent, wherein the vehicle or diluent is selected from the group consisting of water, buffer, saline, serum and other body fluids, and any combinations thereof. The collagen used in the method herein is isolated from the adipose tissue by a method described previously hereinabove. In another aspect, the fat containing tissue is heterologous tissue. In another aspect, the method further comprises the step of morselizing the tissue prior to reinjection into a host or use in vitro.

DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "collagen" refers to the main protein of connective tissue that has a high tensile strength and that has been found in most multicellular organisms. "Collagen" is a major fibrous protein, and it is also the non-fibrillar protein in basement membranes. It contains an abundance of glycine, proline, hydroxyproline, and hydroxylysine. Currently, collagen types I-XIX have been identified and they differ by the amino acid structure of the alpha chain. However, over 90% of the collagen in the body is collagen type I. The term "collagen" as used herein is also includes all collagen types and any form of collagen, whether native nor not, atelocollagen, insoluble collagen, collagen fibers, soluble collagen, and acid-soluble collagen.

As used herein, the term "adipose tissue" refers to fat including the connective tissue that stores fat and other sources of microvascular tissue in the body such as placenta or muscle. Adipose tissue contains multiple regenerative cell types, including adipose-derived stem cells (ASCs) and endothelial progenitor and precursor cells.

The term "abdominoplasty" as used herein refers to a cosmetic surgery procedure used to make the abdomen more firm. The surgery involves the removal of excess skin and fat from the middle and lower abdomen in order to tighten the muscle and fascia of the abdominal wall. The "liposuction" refers to a cosmetic surgery operation that removes fat from many different sites on the body. Areas affected can range from the abdomen, thighs and buttocks, to the neck, backs of the arms and elsewhere.

The terms "autologous" refers to tissue or cells (collagen as used herein) which originate with or are derived from the recipient or the patient to be treated.

As used herein, the term "extracellular matrix (ECM)" refers to one or more substances that provide the conditions for supporting cell attachment and growth.

The terms "ultrasound" or "ultrasonic" as used herein generally refer to acoustic waves at frequencies beyond the range of human hearing (e.g., frequencies above 20 KHz). The term "sonication" is used generally to denote ultrasonic activation in any form.

As used herein, the term "morselize" or "morselizing" refers to the treatment of a tissue such as fracturing, cracking, comminuting, milling, pulverizing, hacking, rupturing, cutting, disintegrating, all other forms of morselization, or any combination thereof, e.g., a laboratory cutting machine with a precision spinning blade that minces the tissue to improve uniformity of the composition.

The term "amplitude" as used herein refers to the height between one wave crest and one wave trough adjacent thereto. As used herein the term "frequency" refers to the distance between two adjacent wave crests or wave troughs of the differential waveform. The term "pulse" as used herein is used to indicate a discontinuous ultrasonic wave emitted at predetermined time intervals and according to a predetermined frequency.

The present invention describes a system and method of isolation of fibrous tissue, mainly collagen from adipose tissue by the use of sonication. The method of the present invention addresses some of the problems in the prior art associated with collagen isolation. The tissue (fat) to be sonicated is present in a container, flow cell, which will hold the fat and is transparent to ultrasound waves. On sonication the sonicated material is filtered out through the bottom of the flow cell and the sonicated collagen is trapped in the filter, which may be taken for further processing.

Collagen, the key structural protein of the skin, is a perfect choice as dermal filler for various skin imperfections and in the treatment of wrinkles, deep folds (such as nasolabial folds), frown lines and deep scars or similar indentations. It is also useful in augmenting tissue such as in the lips or other tissue deficiencies (both congenital and acquired). Collagen when formed in a sheet can also be used as a supporting tissue for wound healing such as in cleft palate surgery. A wrinkle is a localized loss of collagen, so to treat wrinkles the lost collagen is restored by injecting it back. Collagen has been injected into wrinkles for decades. The various types of collagen injections are described below:

(i) Bovine collagen: Bovine injectable collagen (ZyDerm, ZyPlast, etc.) has been around the longest and is the least expensive. Unfortunately, around 3-7 percent (estimates wary widely) of people develop an allergy due to small but important structural differences between human and bovine collagen more predominantly in patients with connective tissue diseases such as rheumatoid arthritis, systemic lupus erythematosus, scleroderma, and dermatomyositis. Since collagen is gradually degraded by the body's enzymes, the effects tend to disappear after 3-6 month and the treatment must be repeated to maintain results.

(ii) Human collagen: Human injectable collagen (CosmoDerm, CosmoPlast, Autologen, etc.) is similar to bovine collagen in terms of its uses, durability and other properties but has one important advantage: lower risk or allergic and other immune reactions. However, human collagen tends to be more expensive. The sources vary depending on the brand and include human tissue cultures, cadaver tissue obtained at the time of death, and patient's own excess skin removed during cosmetic procedures.

(iii) Human acellular dermal matrix: Human acellular dermal matrix is human dermis stripped of all cells and specially treated to increase stability and reduce the risk of immunological reactions. Acellular dermal matrix is typically obtained from the skin of human cadavers. It is tested for diseases (HIV, hepatitis, etc.), treated to remove all cells and other potentially immunogenic elements and processed into an implantable or injectable form. The donor matrix serves not only as filler but also to provide scaffolding for the recipient's own cells to attach to. This results in better tissues integration and durability. Still, since dermal matrix consists primarily of collagen, it is gradually broken down by collagen-digesting enzymes. Human acellular dermal matrix comes either as a sheet (AlloDerm) or small particle suspension (Cymetra a.k.a. Micronized AlloDerm). The injection lasts only about 6 months on average, i.e. only slightly longer than conventional bovine collagen. It is used mainly for problems like medium wrinkles, lines, and pitted scars.

(iv) Fibroblast injections: As discussed hereinabove both bovine and human, have an important drawback in that the injected collagen is gradually broken up by the proteolytic enzymes and can only be replenished by more injections. An interesting new approach is to inject collagen-producing cells (fibroblasts) instead of collagen itself. If the injected fibroblasts take hold in the skin, they can keep producing collagen for a long time. However, the use of fibroblasts from donor skin is difficult because of tissue rejection problems. One approach under Isolagen® (no longer commercially available) harvest's the patient's own fibroblasts (from a small skin sample), grows them in tissues culture and then injects the into wrinkles and scars.

Thus, as seen for the discussion hereinabove bovine collagen has problems with immune reaction, rejection, and disease transmission and homologous collagen from donors also suffers the same problems. In addition both are not permanent and resorb fairly rapidly. Autologous collagen does not suffer from immune reaction, rejection or purity problems but is of limited availability as it is usually derived from the patient's own skin harvested at the time of other procedures such as a face lift, abdominoplasty, breast reduction, breast lift, or other procedures involving tissue excision.1,2 It is obvious that the amount of skin is limited and the procedure to acquire it extensive. The tissue obtained from the patient during this unrelated procedure must be packaged and sent to a processing lab where the collagen is extracted, sterilized, solubilized, and prepared for re-injection. This process takes 3-4 weeks at a minimum. Autologen is a trade mark for autologous collagen but is not available anymore secondary to the cost and complexity of production.

Another method, trademarked as Isolagen®, consists of harvesting fibrous cells and growing them in a lab and re-injecting them. Again this was time consuming and expensive. In addition the results were disappointing and the processing method is no longer commercially available.

Collagen can be obtained from any tissue, however fat containing tissues (adipose tissue) has a lot of it and thereby provides an easy harvesting source. Because adipose tissue is plentiful and can be harvested under local anesthesia in large quantities it has the potential to provide an abundant source of collagen for facial rejuvenation, regeneration, and tissue engineering.

Known methods of isolating collagen from the extracellular matrix (ECM) include enzymatic digestion with collagenase. However, the enzymatic digestion and other steps are time consuming and complicated, are sensitive to temperature, pH, and purity of reagents and are also expensive. Human tissues have been exposed to electromagnetic, sonic or other energy sources to separate the stromal stem cells with or without dissociating agents. (Higgins et al.—U.S. Patent Application Publication No. 2006/0051865, Imanishi et al.—U.S. Pat. No. 5,870,039, and Pacak et al., *Ultrarapid Purification of Colagen Type I for Tissue Engineering Applications*, Tissue Engineering: Part C, Vol. 17, No. 9, 2011; pp. 879-885) Even ultra-rapid processing techniques take hours to process. Decellularized matrix has been obtained from fat but by combined physical, chemical and enzymatic methods (Choi et al., *Decellularized Extracellular Matrix Derived From Human Adipose Tissue as a Potential Scaffold for Allograft Tissue Engineering. J Biomed Mater Res A*, 2011 Mar. 29).

The ultrasound based isolation technique of the present invention, addresses many of the issues associated with collagen isolation and processing mentioned above and can be adapted to produce collagen from human tissues.

Sound waves have been used to aggregate and disrupt cells. Ultrasound has proven useful in the aggregation of cells as a purification procedure (Kilburn). In this procedure of the present invention cells that are not sufficiently heavy to precipitate out of solution are caused to aggregate by ultrasound.

Figure 1:
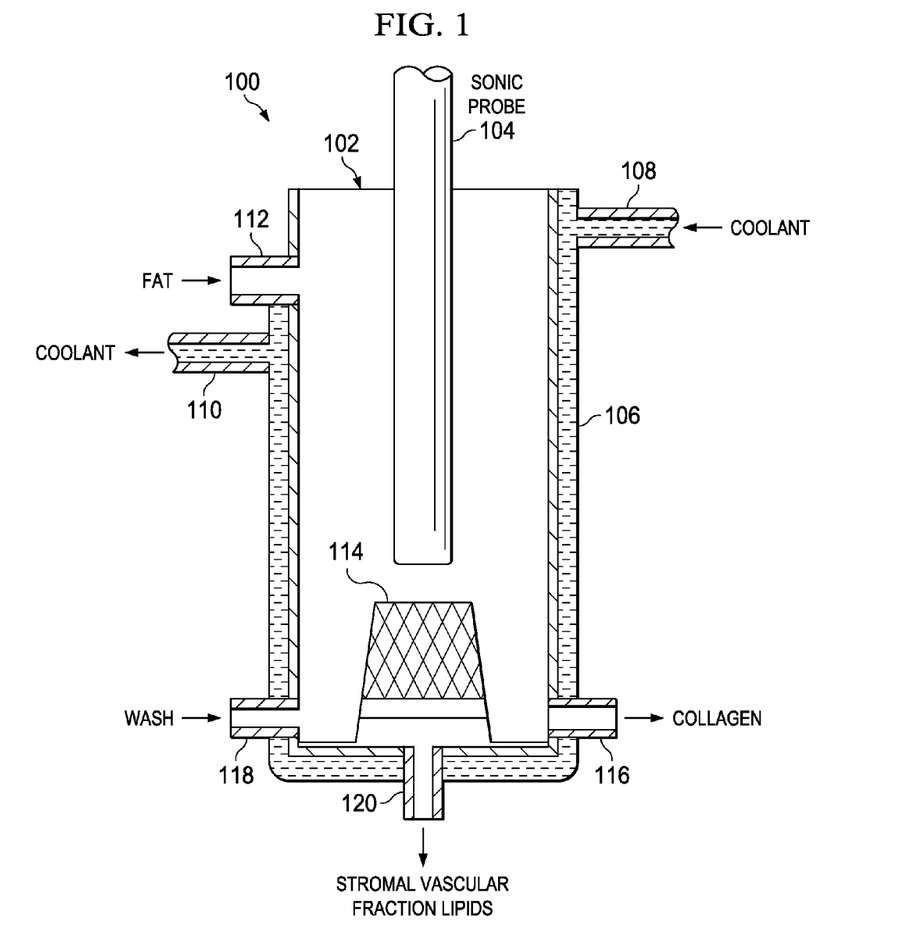
FIG. 1 is a schematic representation of a flow cell adapted for the isolation of collagen from adipose tissue by ultrasound according to one embodiment of the present invention.

The sonication step as described in the preferred embodiment of the present invention was accomplished by sonicating probe. However, it should be appreciated that other types of sonication methods could be used such as acoustic horns, piezo-electric crystals, or any other method of generating stable sound. FIG. 1 is a schematic representation of a flow cell assembly 100 adapted for the isolation of collagen from adipose tissue by ultrasound according to one embodiment of the present invention. Flow cell assembly 100 comprises a jacketed vessel 102 (or a flow cell), with a sonic probe 104. The vessel 102 comprises an outer jacket 106, through which coolant is circulated to cool the vessel 102. Coolant inlet and outlet ports are represented by 108 and 110, respectively in FIG. 1. Inlet 112 represents the port of entry of the fat containing tissue. The vessel 102 contains a filter 114. The fluid passing through the filter contains lipids and cells, the so-called stromal vascular fraction (SVF). The sonicated material (mainly the SVF) is filtered out through the bottom of the flow cell 102, through port 120. The sonicated collagen is isolated by retention on top of the filter 114 and is removed through port 116. The inlet port for introducing a wash solution during the filtration or for cleaning the vessel 102, is represented by 118 in FIG. 1.

In the preferred embodiment described sonication was conducted at 40 kHz for 5 minutes at an amplitude of 80% and a pulse duration of 0.8 seconds using a sonication probe (104) in a custom flow cell (102) with cooling for approximately 50 cc of fat. The flow cell contains (102) a filter (114) of 100 microns but this filter (114) may be as small as 5 microns or as large as 300 microns. Under approximately these same conditions a sonication frequency of, e.g., between 40 and 50 kHz. A fairly wide range of frequencies from subaudio to ultrasound can be used to give sound-enhanced tissue dissociation. Additionally, variations of the type of sonication include continuous versus pulsed sonication.

The tissue (fat) to be sonicated is placed in a container (102) or a flow cell, which will hold the fat and which is transparent to ultrasound waves. The fat can be harvested by liposuction or other techniques such as in an abdominoplasty. To avoid contamination the flow cell is preferably closed. A certain quantity of fat may be placed in the flow cell (102) and then sonicated. Alternatively the fat may be continuously run into the flow cell under sterile conditions and the sonicated material filtered out through the bottom of the flow cell (102). The sonicated collagen is isolated using the filter (114). The fluid passing through the filter contains lipids and cells, the so-called stromal vascular fraction (SVF). The container may be transparent for monitoring or nontransparent. The sonic probe (104) is preferably placed 2 cm from the filter (114) but may be right next to the filter (114) or far away.

Higgins, et al. have described a method to isolate stromal cells from adipose tissue. The adipose tissue may be sonicated and/or enzymatically digested to separate the stromal cells. However, the collagen from the ECM is specifically discarded as described in the Higgins method, "after centrifugation, the collection container together with the filter unit is detached and discarded".

In the present technique, and in contrast with the Higgins method, the fluid is driven through the filter by ultrasonic energy and no centrifugation is needed. The ECM and collagen remains above the filter while the lipids from the fat cells and the SVF passes through the filter. This SVF can then be washed with PBS or other suitable carrier solution. The stromal cell component including adult stem cells can be further concentrated by centrifugation, filtering or separation in an ultrasonic flow cell. The resultant fluid containing lipids and cells can be washed with phosphate buffered saline (PBS).

Figure 2:
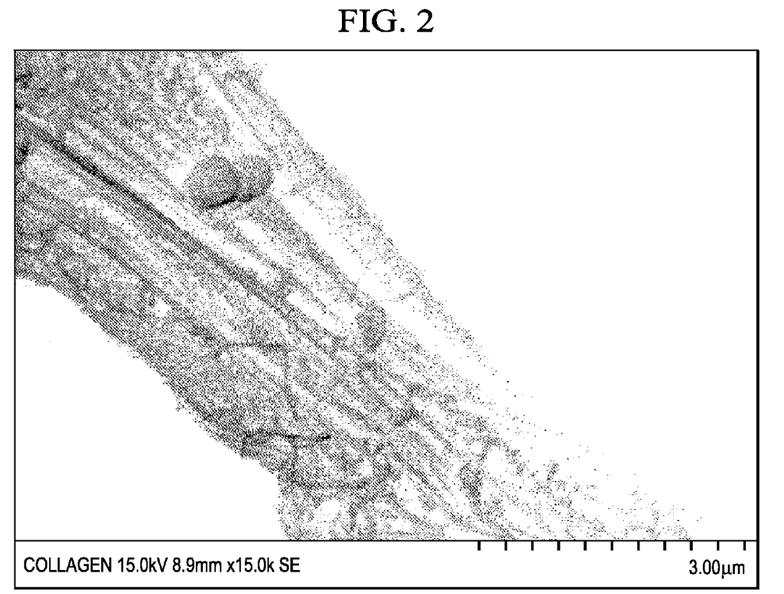
FIG. 2 is a scanning electron micrograph (SEM) images showing collagen fibrils isolated according to the method and apparatus of the present invention.

FIG. 2 is a scanning electron micrograph (SEM) images showing collagen fibrils isolated according to the method and apparatus of the present invention. The collagen isolated by the method of the present invention can be used itself or can be used as a composition comprising one or more additives that may or may not be pharmacologically active. The isolated collagen may be immediately used as is or after reconstitution or it may be stored for use at a future date by cryo-preservation or other techniques. One or more preservatives may be added to the isolated collagen for storage purposes. Non-limiting examples of some additives that may be used include growth and stimulating agents selected from epidermal growth factor, fibroblast growth factor, nerve growth factor, keratinocyte growth factor, platelet derived growth factor (PDGF), fibroblastic growth factor (FGF), vasoactive intestinal peptide, vascular endothelial growth factor (VEGF), stem cell factor, bone morphogenic proteins, chondrocyte growth factor and combinations thereof, analgesic drugs, hemostatic drugs, antibiotic drugs, antioxidants, heparin, anti-inflammatory drugs, local anesthetics and the like to enhance the acceptance of the implanted particulate material, tissue formation agents, adipose tissue formation agents, transforming growth factor, transforming growth factor-β, connective tissue activating peptides, β-thromboglobulin, insulin-like growth factors, tumor necrosis factors, interleukins, colony stimulating factors, erythropoietin, nerve growth factors, interferons, stem cells selected from mesenchymal stem cells, epidermal stem cells, cartilage stem cells, adipose derived stem cells (ASCs), hematopoietic stem cells, and any combinations thereof.

The collagen can then be combined with a suitable carrier for re-injection to correct various tissue defects such as wrinkles. Suitable carriers may be selected from saline, PBS, serum or the SVF obtained from above. In the preferred method the collagen obtained from the method described hereinabove or any other method is combined with a suitable percent of SVF, which is preferably 20% but may be from 10% to 60%. The collagen forms a carrier for the stem cells and also acts as a filler and matrix for new collagen production when injected into the desired area of the host.

Autologous injectable collagen. The process of the present invention involves harvesting adipose tissue using lipoaspirate as the source material, taken from a liposuction surgical procedure. The lipoaspirate shall be packaged and transported to the approved tissue laboratory, processed to isolate the collagen material using a mechanical ultrasonic cavitation method to segregate the collagen fibers from the host material and then the collagen shall be cryo-preserved in order to bank the tissue for future release back to the surgeon for re-injection into the patient that provide the donor tissue.

Tissue Collection and Transport. A liposuction procedure is scheduled and a sample of lipoaspirate is collected using validated instrumentation that pre-filters much of the waste product within the lipoaspirate, common to surgical procedures in which a lipoaspirate is collected, whereby the yield is concentrated adipose tissue. Hereinafter the pre-filtered, concentrated, lipoaspirate is referred to as Processed LipoAspirate (PLA).

A target volume of PLA to be collected can be but is not limited to, e.g., 300-600 ml in volume. The PLA can be injected with a 60 ml syringe into the collection bag and the PLA sealed within. One source for the collection bag is Veris Medical, Menlo Park, Calif., U.S.A. The collection bag can be packaged in validated transportation materials provided by, e.g., Veris Medical, and the collection kit can be shipped at, e.g., room temperature via overnight carrier to a Tissue Lab.

Receipt of Tissue at Lab. The Tissue Lab receives the sample and logs it into the validated database through, e.g., a bar code database. The sample is handled with sterile technique as it is processed as described herein.

Transfer Sample into Processing Chamber. A dose of approximately 200 ml of PLA is transferred into a processing vessel (PV) (which can be obtained from Veris Medical) using a 60 ml syringe. The PV includes an upper chamber and a filter/drain section, which can coupled to a waste collection vessel.

The PV can be installed in the Ultrasonic Cavitation Chamber (UCC)(Veris Medical) and can be disposed of after processing the entire volume of the PLA from the specific patient sample. Note: the processing can be performed in 200 ml increments.

The PV is designed to be used within the UCC, where it can provide a consistent volume of PLA to be processed and consistent filtering that operates under negative pressure (vacuum) to evacuate the waste product while the processing takes place by the UCC.

Segregation Process. The UCC can include a sterile ultrasonic probe matched to the PV whereby the energy dispersion is proved to provide consistent and reliable cavitation of the adipose tissue. The UCC can operate at a cycle of approximately 4 minutes per 200 ml volume of PLA at specific ultrasonic frequency and amplitude settings. The UCC can also be set in a pulsed mode, which provides consistent processing of the PLA. As the fat cells are cavitated, the waste oils and other cells can pass through the filter chamber as the vacuum pressure draws the waste into the waste collection vessel. At the end of the cycle, the majority of the remaining tissue within the PV is collagen fibers.

Pre-Wash. A 60 ml wash of phosphate buffered saline (PBS) can be introduced into the VPV while the filter chamber is under vacuum. Vacuum can be discontinued after 20 seconds.

Introduce PBS and Shear. The collagen can be transferred from the PV into a 30 ml conical centrifuge tube and 20 ml of PBS can be introduced. The collagen/PBS mixture can be transferred into a high-shear mixer and processed to produce a consistent particle size.

Drain and Centrifuge. The PBS solution can be drained from the collagen using a 100 micron conical filter under vacuum. Add 20 ml of PBS back to collagen. The specimen can be centrifuged at approximately 1,200 rpm for 3 minutes.

Final Drain and Introduce Carrier Solution. The PBS solution can be drained from the collagen using a 100 micron conical filter under vacuum. PBS can be added in a volumetric ratio of 0.6 cc of collagen to 0.4 cc of PBS.

Transfer into Final Package and Seal. Transfer final material into 2 cc cryo-preservation vessels and seal per manufacturer protocol. Label specimen and transfer into cryo-preservation protocol.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 5,261,612: Method and Apparatus for Extracting Injectable Collagen from Adipose Tissue.
U.S. Pat. No. 7,588,732: An Autologous Tissue Harvesting and Irrigation Device.
U.S. Patent Publication No. 20110020864: Preparation of High Purity Collagen.
U.S. Pat. No. 6,933,326: Particulate Acellular Tissue Matrix.
U.S. Patent Publication No. 20110020271: Elastin for Soft Tissue Augmentation.

1. Sclafani A P, Romo T, Parker A, Mccormick S A, Cocker R, Jacono A. Autologous collagen dispersion (Autologen) as a dermal filler: clinical observations and histologic findings. Arch Facial Plast. Surg. 2000 January-March; 2(1):48-52.
2. Apesos J, Muntzing M G, Autologen, Clin Plast Surg. 200 October; 27(4):507-10.
3. Pacak C A, Powers J M, Cowan D B. "Ultra-rapidpurification of collagen Type I for Tissue Engineering Applications". Tissue Eng Part C; methods 2011 Apr. 13.
4. Choi, J S et al "Decellularized extracellular matrix derived from human adipose tissue as a potential scaffold for allograft tissue engineering. J Biomed Mater Res A, 2011 Mar. 29.
5. Kilburn, D G et al, "Enhanced sedimentation of mammalian cells following acoustic aggregation," Biotechnol. Bioeng. 34:559-62 (1989).

The invention claimed is:

1. A method for isolation of one or more connective tissue proteins from one or more fat containing tissues comprising the steps of:
harvesting the fat containing tissue obtained by liposuction, abdominoplasty, or any other fat removal techniques, in a jacketed vessel comprising:
a sonic probe, an outer jacket and a mesh filter, wherein the sonic probe and the mesh filter are inside the jacketed vessel, wherein the jacketed vessel further comprises:
a first inlet that allows passage of the one or more fat containing tissue into an interior of the jacketed vessel, which comprises a cooling jacket comprising a cooling inlet and a cooling outlet, wherein the sonic probe in the jacketed vessel capable of generating an acoustic pulses capable of disrupting the fat containing tissue in the jacketed vessel, a mesh filter capable of separating stromal vascular lipids in the jacketed vessel by filtration and in fluid communication with a first outlet, a second inlet in fluid communication with the interior of the jacketed vessel for a washing fluid during the filtration, and a second outlet in fluid communication with the interior of the jacketed vessel for isolation of isolated connective tissue protein by the filtration;
flowing the fat containing tissue into the jacketed vessel, wherein the jacketed vessel is an acoustically permeable closed system;
exposing directly the fat containing tissue to one or more acoustic pulses in the jacketed vessel to separate the one or more connective tissue proteins from a stromal vascular fraction (SVF), wherein the SVF comprises lipids, cells, or any other extracellular elements pass through the mesh filter; thereby isolating the separated connective tissue proteins from the fraction that did not traverse the mesh filter.
2. The method of claim 1, wherein the isolated connective tissue protein comprises collagen type I.
3. The method of claim 1, wherein the one or more fat containing tissues is adipose tissue.
4. The method of claim 1, wherein the acoustic pulses comprise ultrasonic waves.
5. The method of claim 1, wherein the method of isolating the connective tissue proteins is performed under sterile conditions.

6. The method of claim 1, wherein a frequency for the one or more ultrasonic pulses ranges from 40-500 kHz.

7. The method of claim 1, wherein a pore size of the filter ranges from 5 microns-300 microns.

8. The method of claim 1, wherein the fat containing tissue is heterologous tissue.

9. The method of claim 1, further comprising the step of morselizing the isolated connective tissue proteins.

10. A method for isolation of one or more connective tissue proteins from one or more fat containing tissues harvested by liposuction, abdominoplasty, or any other fat removal techniques comprising the steps of:
   introducing the fat containing tissue comprising the one or more connective tissue proteins into a jacketed vessel, the jacketed vessel comprising:
   a sonic probe, an outer jacket and a mesh filter, wherein the sonic probe and the mesh filter are inside the jacketed vessel, wherein the jacketed vessel further comprises:
   a first inlet that allows passage of the one or more fat containing tissue into an interior of the jacketed vessel, which comprises a cooling jacket comprising a cooling inlet and a cooling outlet, wherein the sonic probe in the jacketed vessel is capable of generating acoustic pulses capable of disrupting the fat containing tissue in the jacketed vessel, a mesh filter capable of separating stromal vascular lipids in the jacketed vessel by filtration and in fluid communication with a first outlet, a second inlet in fluid communication with the interior of the jacketed vessel for a washing fluid during the filtration, and a second outlet in fluid communication with the interior of the jacketed vessel for isolation of isolated connective tissue protein by the filtration;
   acoustically separating the connective tissue proteins from the fat containing tissues in the jacketed vessel; thereby isolating in the jacketed vessel the separated connective tissue proteins by filtration from a fraction that did not traverse the mesh filter.

11. The method of claim 10, wherein the isolated connective tissue protein comprises collagen type I.

12. The method of claim 10, wherein the one or more fat containing tissues is adipose tissue.

13. The method of claim 10, wherein the acoustic pulses comprise ultrasonic waves.

14. The method of claim 10, wherein the method of isolating the connective tissue proteins is performed under sterile conditions.

15. The method of claim 10, wherein a frequency for the one or more ultrasonic pulses ranges from 40-500 kHz.

16. The method of claim 10, wherein a pore size of the filter ranges from 5 microns-300 microns.

17. The method of claim 10, wherein the fat containing tissue is heterologous tissue.

18. The method of claim 10, further comprising the step of morselizing the isolated connective tissue proteins.

19. A method for isolation of one or more connective tissue proteins from one or more fat containing tissues comprising the steps of:
   harvesting the fat containing tissue by liposuction, abdominoplasty, or any other fat removal techniques, in a jacketed vessel comprising:
   a sonic probe, an outer jacket and a mesh filter, wherein the sonic probe and the mesh filter are inside the jacketed vessel, wherein the jacketed vessel further comprises:
   a first inlet that allows passage of the one or more fat containing tissue into an interior of the jacketed vessel, which comprises a cooling jacket comprising a cooling inlet and a cooling outlet, wherein the sonic probe in the jacketed vessel is capable of generating acoustic pulses capable of disrupting the fat containing tissue in the jacketed vessel, a mesh filter capable of separating stromal vascular lipids in the jacketed vessel by filtration and in fluid communication with a first outlet, a second inlet in fluid communication with the interior of the jacketed vessel for a washing fluid during the filtration, and a second outlet in fluid communication with the interior of the jacketed vessel for isolation of isolated connective tissue protein by the filtration;
   flowing the fat containing tissue into the jacketed vessel, wherein the jacketed vessel is an acoustically permeable closed system;
   exposing directly the fat containing tissue to one or more acoustic pulses at between 40-500 kHz in the jacketed vessel to separate the one or more connective tissue proteins from a stromal vascular fraction (SVF), wherein the SVF comprises lipids, cells, or any other extracellular elements pass through the mesh filter; thereby isolating the separated connective tissue proteins from the fraction that did not traverse the mesh filter.

20. The method of claim 19, wherein the isolated connective tissue protein comprises collagen type I.

21. The method of claim 19, wherein the one or more fat containing tissues is adipose tissue.

22. The method of claim 19, wherein the acoustic pulses comprise ultrasonic waves.

23. The method of claim 19, wherein the method of isolating the connective tissue proteins is performed under sterile conditions.

* * * * *